United States Patent [19]

Wilson

[11] 4,315,421

[45] Feb. 16, 1982

[54] METHOD OF CONTROLLING THE CONCENTRATION AND STABILITY OF AN EMULSION

[75] Inventor: Walter A. Wilson, Pittsburgh, Pa.

[73] Assignee: National Steel Corporation, Pittsburgh, Pa.

[21] Appl. No.: 100,206

[22] Filed: Dec. 4, 1979

Related U.S. Application Data

[62] Division of Ser. No. 948,626, Oct. 3, 1978, Pat. No. 4,202,193.

[51] Int. Cl.³ .................... B21B 27/10; B21B 45/02; G05D 11/06
[52] U.S. Cl. .................................. 72/42; 72/236; 137/92
[58] Field of Search ...................... 72/41–45, 72/201, 236; 73/53, 61.1 R; 137/3, 88, 89, 91, 92; 252/49.5

[56] References Cited

U.S. PATENT DOCUMENTS

| | | | |
|---|---|---|---|
| 2,850,552 | 9/1958 | Ogle | 137/91 X |
| 3,074,277 | 1/1963 | Hill | 137/3 X |
| 3,153,420 | 10/1964 | Roberts | 137/89 |
| 3,249,115 | 5/1966 | Young | 137/92 |
| 3,254,965 | 6/1966 | Ogle | 137/92 X |
| 3,275,018 | 9/1966 | Roberts | 137/92 X |
| 3,583,209 | 6/1971 | Banks | 73/32 A |
| 4,024,742 | 5/1977 | Vucich et al. | 72/42 |

Primary Examiner—Ervin M. Combs
Attorney, Agent, or Firm—Paul T. O'Neil; James L. Bean

[57] ABSTRACT

A method of and system for controlling the oil concentration in and the stability of an oil-in-water emulsion used as a coolant-lubricant in a metalworking operation in which a portion of the emulsion is circulated through a sensor to monitor its density and to generate a signal relating the density to the oil concentration. The signal is employed to control addition of oil to the emulsion to thereby control the concentration within close limits. Sensing means also monitors the stability of the circulated emulsion, and emulsifier is added, as required, either to the oil to be added or directly to the emulsion to thereby control both the oil concentration in and the stability of the emulsion.

23 Claims, 4 Drawing Figures

METHOD OF CONTROLLING THE CONCENTRATION AND STABILITY OF AN EMULSION

This is a division of application Ser. No. 948,626, filed Oct. 3, 1978, now U.S. Pat. No. 4,202,193, the entire disclosure of which is incorporated herein by reference.

BACKGROUND OF THE INVENTION

1. Field of the Invention

This invention relates generally to oil-in-water emulsions employed as lubricants in metalworking operations, and more particularly to a method of and apparatus for monitoring the emulsion stability and oil concentration and for controlling the addition of oil and emulsifiers to thereby control the concentration and stability of the emulsion.

2. Description of the Prior Art

It is well-known to use oil-in-water emulsions as lubricants in metalworking operations. For example, in operation of rolling mills to shape metal such as aluminum and steel, it is conventional practice to employ an oil-in-water emulsion to flood the work rolls and the metal being shaped as it enters the rolls. In such uses, the emulsion acts both as a lubricant and as a coolant for both the work and the rolls. Such emulsions are also conventionally used in cutting, machining, milling, drawing, grinding and other like metalworking operations where both lubrication and temperature control may be important considerations. The present invention was developed in connection with operation of a steel rolling mill and reference to the operation of such a mill will from time to time be made herein in describing the invention. It is understood, however, that the invention is not limited to such a system, but rather is equally applicable to systems for use in other metal-working operations.

A typical oil-in-water emulsion utilized in a steel rolling operation may comprise an aqueous dispersion of a blend of oils, usually a mineral oil with natural oils such as tallow, along with nonionic and/or anionic emulsifying agents. The emulsion may also contain minor amounts of other ingredients such as bacteriocides and coupling agents which are employed to increase the useful life of the emulsion. A disclosure of such emulsions may be found in numerous prior art publications, such, for example, as U.S. Pat. Nos. 3,783,664 and 3,409,551.

In operation of a rolling mill, an oil-in-water emulsion is conventionally flowed or sprayed onto the work and/or rolls ahead of each set of work rolls. This necessarily results in a loss of a portion of the emulsion due to evaporation, drag-out, spillage, and the like. Variations in temperature of the metal, work rolls and ambient air can produce variations in evaporation rate, particularly of the water component of the emulsion, and various factors including surface conditions of the rolls and the metal being worked affect the loss of water, oil, emulsifiers, and other components. Thus, in order to maintain a consistent oil concentration and emulsion stability, it is necessary to periodically add varying amounts of oil, emulsifiers, and water to the system.

The cooling and lubricating systems employed with rolling mills generally are either of the direct-application type, most frequently employed with specialty orders and short runs, or of the recirculating or reclaiming type. The reclaiming lubrication systems employed with steel rolling mills typically include a large-volume storage chamber, or tank, which may incorporate means for controlling the temperature of the emulsion in the system. Emulsion pumped from this tank to the mill cools and lubricates the workpiece and rolls, then flows downnwardly and is collected in a sump beneath the work rolls. The collected emulsion is then purified through suitable filters, screens, and the like before being returned to the storage tank for recirculation. Such systems may have a capacity of many thousands of gallons, and the emulsion in the system may be recirculated and used for several months of substantially continuous operation. However, it is necessary to periodically analyze samples of the emulsion to determine the oil concentration and emulsion stability, as well as other factors such as PH, bacteria count and the like. Depending on the results of the sample analysis, make-up water, oil, emulsifiers and other components are added to control the stability, oil concentration, and other characteristics within prescribed limits.

Direct application systems generally have a substantially lower total emulsion capacity and do not incorporate the sophisticated reclaiming and purifying means employed in recirculating systems. Instead, re-use of the used emulsion is accomplished by pumping the used emulsion from the sump to a holding and mixing tank where it is continuously agitated or mixed to prevent separation and from which it is pumped back to the point of application. Again, however, the composition and stability of the emulsion must be maintained within prescribed limits and this is accomplished by the periodic addition of oil, water, emulsifiers, and the like. As a general rule, the emulsion in a direct application system is discarded after use for a comparitively short time such as after a specified number of turns or after completion of a particular order or job.

In the past, it has been conventional practice to periodically draw emulsion samples for laboratory-testing to determine oil concentration and emulsion stability. The concentration has generally been determined by centrifuging or by salt-split testing, both procedures being well-known in the art. The stability of the emulsion is represented by an emulsion stability index (ESI), which may be determined by conventional test procedures such as those contained in ASTM 3342-74, and which is an indication of the rate of separation of the oil and water phases in a quiescent emulsion.

It has also been proposed to flow a portion of an emulsion through a continuous centrifuge to separate the oil and water components which are then caused to flow through separate flow meters which generate signals proportional to the flow of the two components. A comparison of the two signals is employed to periodically add slugs of oil, as required, to maintain the proper concentration of oil in the emulsion. Such a system is disclosed in U.S. Pat. No. 3,153,420.

U.S. Pat. No. 3,954,119 discloses a system for controlling the oil concentration in an emulsion by measuring the rate of propagation of ultrasonic vibrations through the emulsion flowing in a pipe and relating this measured rate to the emulsion density, and thereby emulsion concentration. The propagation rate is utilized to control the addition of oil and water to maintain the proper oil concentration in the emulsion.

SUMMARY OF THE INVENTION

According to the present invention, a rolling mill is provided with an oil-in-water emulsion lubricating system in which the oil concentration may be selected and automatically controlled at the selected value, with a continuous record being provided of the concentration of the oil in the system. At the same time, the stability of the emulsion can be automatically determined at preselected, frequent intervals, and emulsifiers added to the make-up oil or directly to the emulsion to maintin the ESI within prescribed limits.

A portion of the emulsion is pumped through a density cell unit, for example a Dynatrol liquid measuring density cell, which continuously determines the density of the solution and generates a signal proportional to this density. The emulsion discharged from the density cell is returned directly to the emulsion supply system, and the signal is fed to a continuous density recording and controlling system having means for preselecting and setting the density, or oil concentration to be maintained. A conventional, commercially available L&N recorder having an adjustable control set point may be employed to simultaneously record the oil density, on a continuous basis, and to supply a signal, through a conventional controller, to a motor control for controlling the operation of an oil metering pump to supply make-up oil, as required to the system.

A Dynatrol liquid density cell employs a U-shaped tube through which the emulsion to be tested is pumped. The U-shaped tube is excited, and the amplitude of the displacement is carefully measured and employed as an indication of the density of the fluid contained in the tube. Dynatrol density cells, per se, are commercially available and as such form no part of the present invention.

In the conventional installation employing a Dynatrol density cell, the unit is mounted with the U-shaped tube in the horizontal direction. However, by mounting this unit with the tube in the vertical direction with the open end of the "U" directed upward, in accordance with the present invention, the unit may also be employed to determine the stability of the emulsion. This is accomplished by periodically stopping the flow of emulsion through the unit and permitting the oil and water in the U-tube to separate for a fixed length of time. At the conclusion of this fixed time, the density of the fluid in the U-tube is determined, and the change in density is employed to calculate the emulsion stability index by use of a mean time stability calculator. The stability calculator generates a signal which may be employed to energize a digital readout display and also to control the actuation of an emulsifier pump to add a metered amount of emulsifiers to the oil which is supplied to the emulsion to maintain the concentration. Alternatively, the emulsifier may be added directly to the emulsion as in the emulsion mixing tank. The emulsion stability controller also employs a set point control which may be adjusted to maintain the desired ESI.

According to the present invention, the necessity for repeatedly drawing samples of the emulsion for laboratory testing is eliminated. At the same time, a continuous permanent recording of the emulsion concentration is provided and the emulsion stability index is displayed on a visual readout in the oil room. Thus, not only is the concentration and stability automatically maintained within very close limits, but the visual display facilitates monitoring the system and a permanent record is provided for subsequent correlation and evaluation of the mill product.

BRIEF DESCRIPTION OF THE DRAWINGS

The foregoing and other features and advantages of the present invention will become more apparent from the detailed description contained herein, taken in conjunction with the drawings, in which.

DESCRIPTION OF THE PREFERRED EMBODIMENTS

Figure 1:
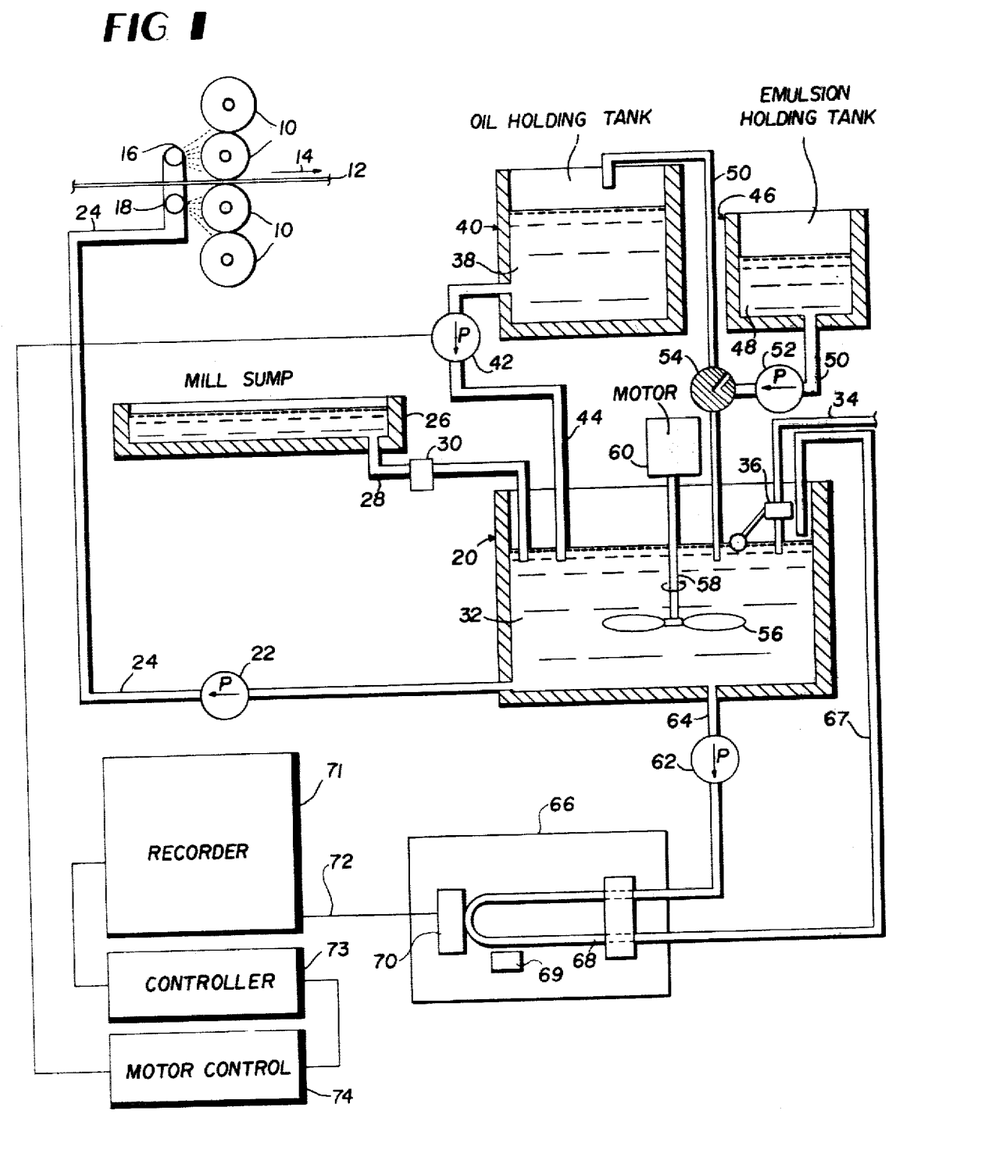
FIG. 1 is a schematic illustration of a portion of a direct application lubrication system used to supply an oil-in-water emulsion to a rolling mill and incorporating means for controlling the oil concentration in the emulsion.
Figure 2:
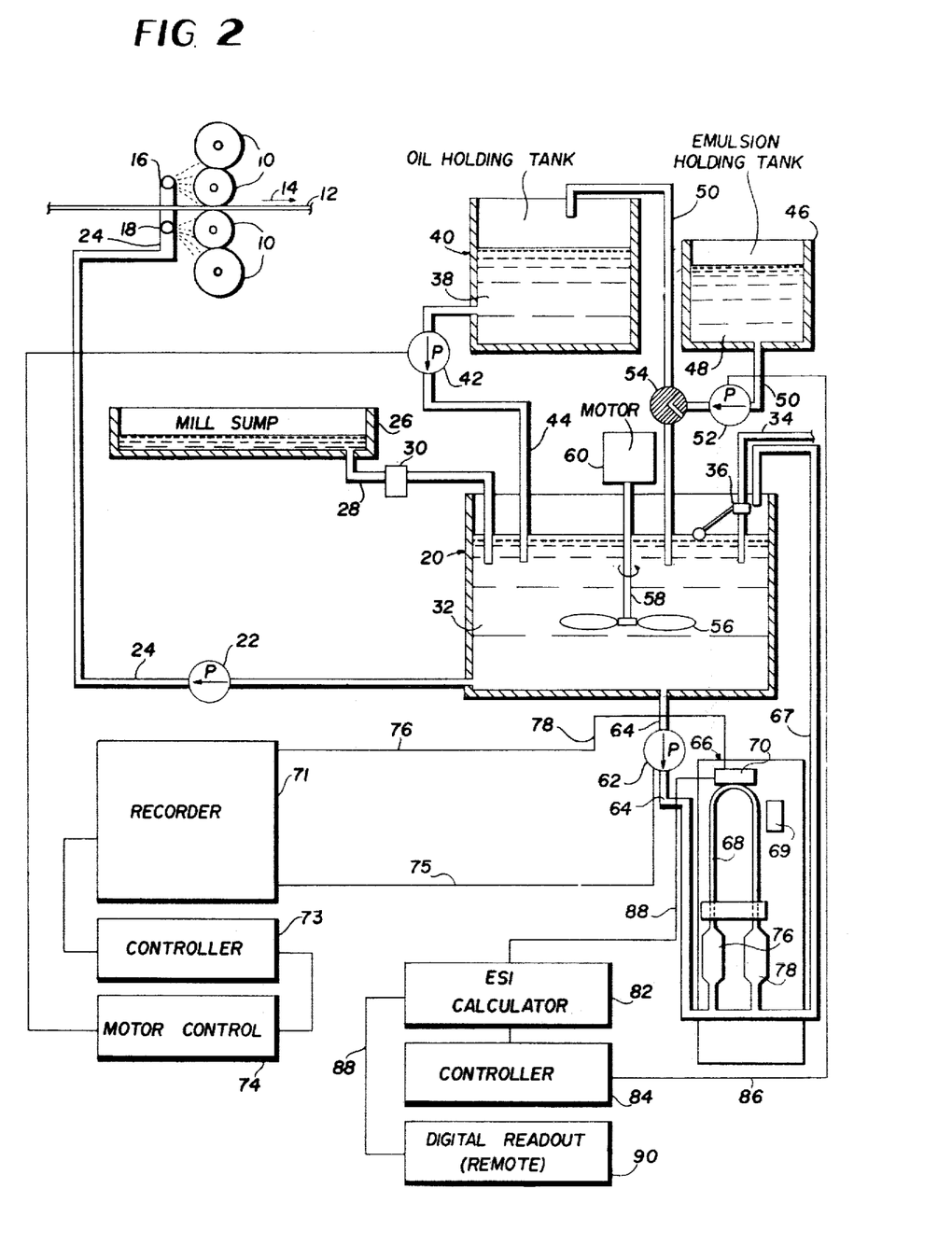
FIG. 2 is a schematic illustration of a system similar to FIG. 1 and further including means for controlling the stability of the emulsion.

Referring to the drawings, FIGS. 1 and 2 schematically illustrate a cooling and lubricating system for supplying an oil-in-water emulsion to the work rolls of a four-high rolling mill of the type employed, for example, in cold rolling steel or aluminum sheet. The set of work rolls and back-up rolls are designated generally by the reference numeral 10, with a strip of metal 12 being illustrated as passing through the nip of the work rolls in the direction of the arrow 14. Upper and lower manifolds 16, 18, respectively, are supported in position ahead of each set of work rolls in the rolling mill to continuously flow or spray the cooling and lubricating emulsion onto the surface of the strip and work rolls as the strip enters each roll stand. The cooling and lubricating emulsion (hereinafter emulsion) is supplied from an emulsion mixing tank 20 by a pump 22 connected in pipe 24 to the manifolds 16, 18. The portion of the emulsion which is not evaporated by the heat of the strip and work rolls or carried away by the strip, flows over the edge of the strip and down into a mill sump 26 positioned below each roll stand 10 in the mill. Used emulsion collected in the mill sump 26 is then returned to the mixing tank 20 through pipe 28 and suitable filters indicated generally at 30.

The composition of the emulsion 32 contained in the mixing tank 20, and in the circulating system, may vary depending upon the nature of the metal working operation and normally will comprise an aqueous dispersion of a blend of oils and emulsifying agents to which small amounts of other ingredients such as bacteriocides and coupling agents are added. The level of the emulsion is maintained in tank 20 by the addition of water from a suitable source, not shown, through a conduit 34 and ball float valve 36 and oil 38 from a holding tank 40 by a metering pump 42 connected in pipe 44 extending from the holding tank 40 to the mixing tank 20.

Emulsifiers may be added to the oil in the holding tank or alternatively may be added directly to the mixing tank, as required, to provide a stable emulsion. An emulsifier holding tank 46 for containing a supply 48 of an emulsifying agent or a suitable blend of emulsifying agents (hereinafter,, emulsifier) is connected to the oil holding tank by a pipe 50, and a metering pump 52 connected in pipe 50 is operable to deliver metered quantities of emulsifier to tank 40. Alternatively, the emulsifiers may be delivered directly from tank 46 to the mixing tank 20 and mixed with the emulsion in the holding tank when required. To accomplish this, pump 52 may be connected in pipe 50 through a two-way valve 54 which may be selectively operable to direct the pump discharge either to tank 40 or tank 20. Operation of pump 52 may be manually controlled, or alternatively it may be automatically controlled in the manner described hereinbelow with reference to FIG. 2.

The emulsion 32 in mixing tank 20 is continuously stirred and agitated during operation of the mill by a fan-like blade or propeller 56 supported on a shaft 58 operatively connected to a motor 60 mounted above the tank 20. The continuous agitation of the liquid maintains the oil dispersed throughout the water in very fine droplets, with the emulsifier acting to break up the oil in the conventional manner.

As previously described, a portion of the emulsion delivered through manifolds 16 and 18 to the metal working apparatus will inevitably be lost so that it is necessary to periodically add quantities of the various components of the emulsion to make-up for the loss. However, since the various factors affecting loss of the emulsion may themselves vary, the individual ingredients of the emulsion must be added in varying quantities from time to time in order to maintain the original, or desired composition of the emulsion. For example, an increase in temperature will produce an increased rate of loss of the water phase of the emulsion through evaporation whereas a variation in the composition or surface characteristics of the metal being rolled can vary the rate of carryout of the oil phase. In accordance with the present invention, the oil concentration in the emulsion is continuously monitored and automatically maintained at a predetermined level. This is accomplished by pumping emulsion from the mixing tank 20 through an oil concentration meter or cell which continuously measures the density of the solution and generates a signal proportional to the measured density. The emulsion discharged from the cell is returned directly to the mixing tank, and in accordance with the invention, the signal from the cell is employed to control the oil concentration in the emulsion within specified limits and to provide a continuous record of the concentration.

As shown in FIGS. 1 and 2, a pump 62 is connected in supply pipe 64 between the mixing tank 20 and a liquid density measuring cell 66 which, in turn, has its outlet connected to a return pipe 67 leading back to tank 20. Thus, emulsion may be continuously circulated by the pump 62 from the mixing tank through the concentration cell 66 and returned directly to the mixing tank. Oil concentration cell 66 is preferably a commercially available Dynatrol density cell, for example a Dynatrol type CL 10HY density cell employing a normally horizontally mounted stainless steel U-tube 68 through which the liquid whose density is to be determined is flowed. In the embodiment of FIG. 1, the cell 66 is mounted in its normal position with the open ends of the U-shaped tube being rigidly supported and the closed loop end of the "U" being unsupported. The closed end is excited at a fixed frequency, e.g., 120 Hz., by a suitable coil 69 with the liquid flowing through the cell, and the amplitude of the tube displacement is accurately measured by a pick-up 70 which generates an electric signal that is a function of the measured tube displacement. The mass of the liquid flowing in the tube directly affects tube displacement so that measured displacement can be directly related to the liquid mass or density and consequently the oil concentration in the emulsion.

The electrical signal generated by the density cell 66 is fed through line 72 to a continuous recorder 71 calibrated to provide a continuous, permanent record of the oil concentration in the emulsion as determined by the density cell. Recorder 71 may be an L&N Speedomax H strip chart recorder, manufactured by Leeds and Northrop Corporation, having a chart speed of two inches per hour and a response time of five seconds. Such a recorder is commercially available and has provision for adjusting the zero and span which may be set to accurately reflect the zero percent emulsion and a reading near the maximum, for example an umulsion containing 14% oil, as determined by centrifuging. The zero dial reading may be set to zero when only the water employed in the emulsion is flowing through the density cell 66. The zero setting may be quickly checked and adjusted as necessary to compensate for variations in density of the water supply.

The recorder 71 also includes an adjustable control set point which may be set to the desired oil concentration, and any deviation between the set point and the actual oil concentration as determined by the density cell 66 will result in recorder 71 producing an electrical signal producing an imbalance in a control circuit in a controller 73 which, in turn, directs a signal to motor control 74 controlling the operation of pump 42. Controller 73 may be an L&N Series 80 controller, and motor control 74 may be a Dynatrol motor control employed to control operation of the motor, for example, an eddy current AC motor, driving the metering pump 42 through a suitable gear reducer. Since such motors and gear reducers are conventional elements in driving metering pumps such as the pump 42, they are not illustrated in the schematic drawings of FIGS. 1 and 2.

In operation of the emulsion system shown in FIG. 1, when the signal from the Dynatrol density cell 66 indicates to recorder 71 that the density of the emulsion 32 in mixing tank 20 is below the required level as set in the recorder, an imbalance signal is transmitted to the controller 73 which, in turn, transmits a drive signal to the motor control 74 to drive the metering pump 42 at a rate to provide the desired oil concentration within a relatively short time. The emulsion flowing from oil holding tank 40 flows directly into the mixing tank 20 where the fresh oil is mixed by the continuously operating mixing blade 56. As more oil is added to the emulsion 32, density cell 66 senses the increased concentration and adjusts the recorder 71 to reflect the increase. When the desired concentration is reached, the imbalance signal to controller 73 is cancelled and pump 42 is stopped.

During operation of the system, as the level of emulsion 32 drops in tank 20, fresh make-up water is automatically added directly to the emulsion tank through line 34 and ball float valve 36. The addition of any substantial amount of make-up water is quickly sensed by the density control cell 66 as an increased density, or decreased oil concentration, and additional oil from holding tank 20 is added to bring the concentration of the emulsion to the desired level in the manner just described.

A predetermined quantity of emulsifier 48 from the holding tank 46 may be initially added to the oil in holding tank 40 so that, upon each addition of oil, a proportionate amount of emulsifier is also added to maintain the stability of the emulsion. Alternatively, the emulsifier may be added directly to the emulsion within tank 32 when determined to be necessary, as by taking samples of the emulsion in the manner described above. Two-way valve 54 may be selectively operated to direct the emulsifying agents either to holding tank 40 or to mixing tank 20, as desired.

Referring now to FIG. 2, a modification of the system is illustrated in which the stability of the emulsion is controlled by automatic determination of the ESI and automatic control of the addition of emulsifier to maintain the stability of the emulsion within prescribed limits. In this embodiment of the invention, the density cell 66 is mounted in the vertical direction, i.e., with the internal stainless steel U-tube 68 extending vertically so that emulsion flowing from pump 62 enters the unit and flows upward through one leg, around the closed end, and downward through the other leg of the tube before exiting the unit to return through pipe 67 to the holding tank 20. A timing mechanism in recorder 71 is connected in the control circuit of pump 62 through line 75, and periodically stops operation of the pump so that flow of the emulsion through the density cell 66 is temporarily interrupted with the U-tube remaining filled with emulsion. A pair of sedimentation amplifying emulsion reservoirs 76, 78 are attached one to the bottom open end of each vertically extending leg of the U-tube 68 with the reservoirs extending downwardly below the bottom end of the U-tube. The reservoirs 76, 78 are generally bottle-shaped and have a diameter substantially greater than the diameter of the U-tube 68. Reservoir 76 has its bottom end connected directly to supply pipe 64, and reservoir 78 has its bottom end connected to return pipe 67.

When the flow of emulsion through density cell 66 is stopped, the oil and water phases of the emulsion contained in reservoirs 76, 78 and in the U-tube are permitted to separate, during which time the oil tends to rise in the legs of the U-tube to the closed-loop end and the water tends to settle toward the open ends of the U-tube legs and into the reservoirs. By providing a reservoir of emulsion immediately beneath the open ends of the two legs, the separation effect is amplified since oil separating from the increased volume of the reservoirs will tend to more quickly displace water or emulsion from the smaller diameter U-tube.

During the time that flow through the density cell is stopped, the density is determined by exciting the U-tube in the normal manner. The electrical signal generated by the density cell 66, while the oil and water are separating, is fed through line 80 to an emulsion stability index meantime calculator 82. Calculator 82 compares the density signals from cell 66 to the original density value, and employs this comparison to calculate the mean time required for separation of the oil and water phases of the emulsion. The mean time thus determined may then be employed as an indication of the ESI of the emulsion.

An electrical signal representing the ESI determined by calculator 82 is transmitted to a controller 84 which is connected, through line 86, to the pump 52 to control operation of the pump. Controller 84 is provided with an adjustable set point which may be set to control operation of the pump 52 depending upon the output of the electrical signal from the ESI calculator. Thus, when the calculator determines that the ESI is below the value set on controller 84, controller 84 then actuates the pump 52 to deliver a predetermined volume of emulsifier through valve 54 to the emulsion in tank 20 or alternatively to the oil in holding tank 40.

The signal from the calculator 82 is also led, through line 88, to a digital readout 90 which may be located at a remote position such as in the oil control room to provide a readily visible digital readout representative of the stability index.

After a predetermined time sufficient for completion of the ESI determination, the timing mechanism in recorder 71 returns the system to the normal operating mode by energizing pump 62 and conditioning density cell 66 to feed the continuous electrical signal through line 72 to recorder 71. The timing mechanism in the recorder 71 then maintains the system in this condition to continuously monitor and provide a record of the emulsion density for a predetermined time before returning the system to the mode for checking the emulsion stability as described. For example, the recorder may be set to check the emulsion stability at intervals of eight to ten minutes in a normal metal rolling operation.

In an alternate arrangement, the signal produced by the ESI calculator can be employed only to energize the digital readout to signal the need for the addition of emulsifier, with the addition of the emulsifier being manually controlled.

In a further alternative embodiment of the invention, two density control units may be employed, one connected in the system, as described with respect to FIG. 1, and a second density control unit employed to provide the signal to the ESI calculator. In this arrangement, a continuous record of the oil concentration in the emulsion is provided with a second density cell being employed for the intermittent calculation of the ESI to control the addition of emulsifier, and consequently the stability of the emulsion.

In order to evaluate the invention under actual mill conditions, a Dynatrol density cell of the type described above was installed in a direct application emulsion dispensing system having a 250 gallon mixing tank. The density cell was connected to an L&N strip chart recorder located on the mill floor at a location somewhat remote from the mill. The recorder was calibrated prior to installation in the mill, with the zero and span setting of the cell being determined experimentally utilizing water and oil of the general type employed in the mill emulsion.

Figure 3:
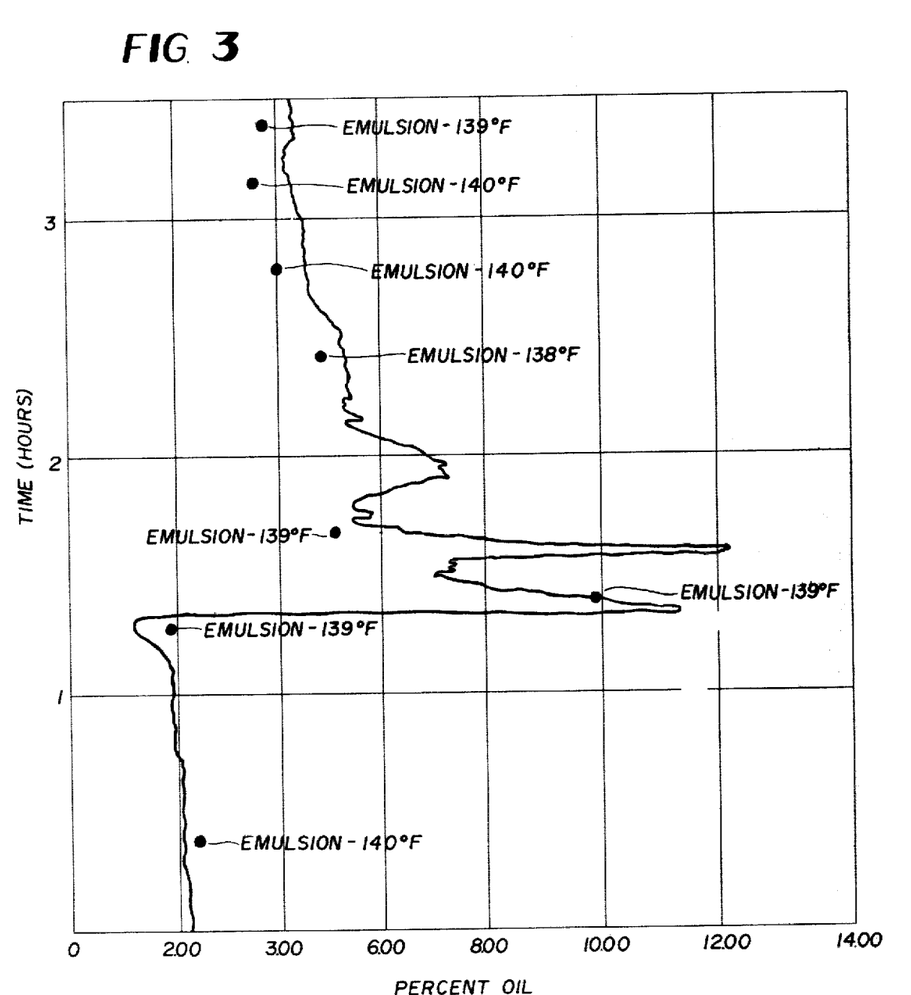
FIG. 3 is a typical recorder trace of the oil concentration as recorded on the apparatus of the present invention, with centrifuge test values superimposed at periodic points for comparison purposes.
Figure 4:
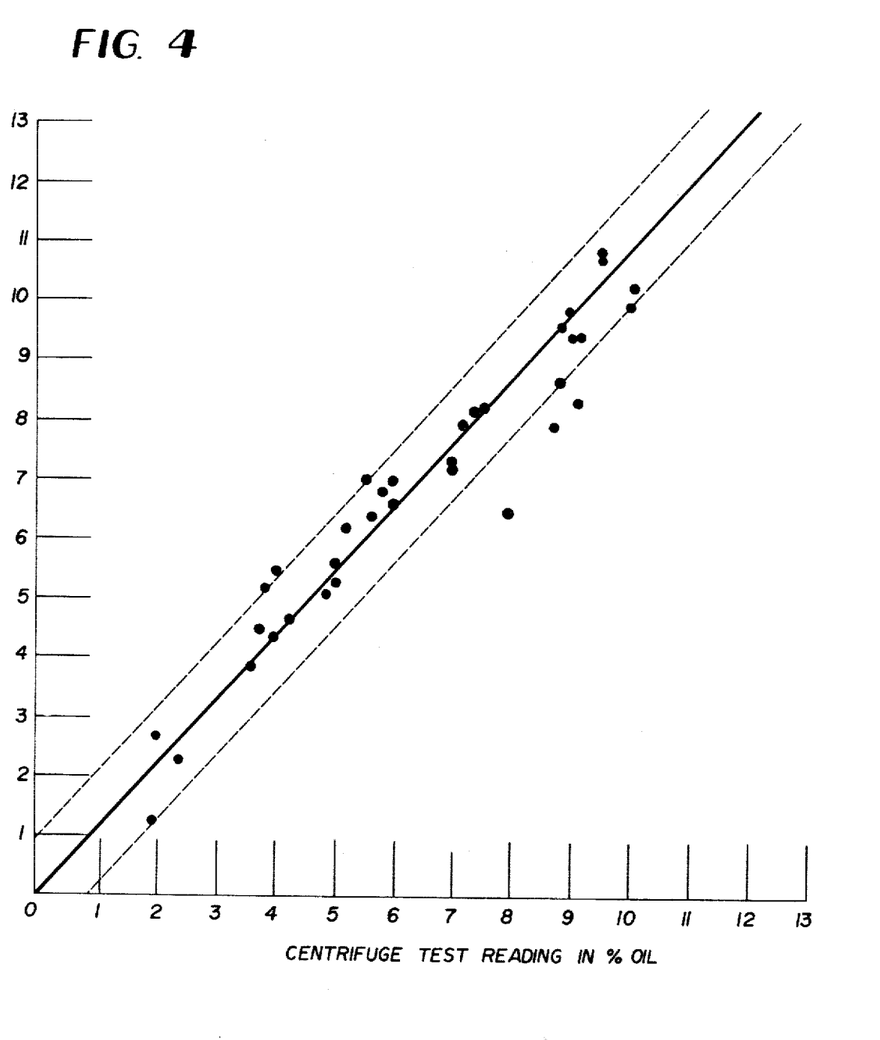
FIG. 4 is a graphic comparison of oil concentration as determined by the apparatus according to the present invention and by centrifuge testing over a range of oil concentrations.

FIGS. 3 and 4 represent typical data collected during the trial run of the system on the mill during use in the cold rolling of strip steel. FIG. 3 represents a typical recorder trace of the oil concentration as determined by the Dynatrol density cell and recorded on the L&N recorder. At various intervals during the operation, samples of the emulsion were taken from the mixing tank and the percent of oil determined by centrifuging, using standard centrifuge procedure. The results of the centrifuge tests, and the emulsion temperature at the same time the samples were taken, are superimposed on the representation of the strip chart recording in FIG. 3.

FIG. 4 represents a correlation between the Dynatrol density cell readings and the centrifuge test values for various oil concentrations in an emulsion of the type employed in actual mill operations and the percent of oil determined by centrifuging. The correlation in FIG. 4 approaches a two-sigma accuracy of ±1.0%. The data was taken from a density cell which had been operated for a period of approximately one month with only two adjustments to the zero setting after initial start-up. The correlation between the Dynatrol cell readings and the centrifuge testing was consistently better than the correlation between centrifuge testing and salt split testing conducted during the same period. Thus, the tests clearly established that the apparatus according to the present invention may be readily employed to continuously monitor and control the oil concentration in an oil-in-water emulsion under continuous mill operating conditions.

Tests conducted under mill operating conditions employing the Dynatrol density cell described above to determine the ESI have also shown the system to be reliable. By utilizing essentially the same equipment for monitoring both the oil concentration and emulsion stability, the stability index can be determined quickly and at frequent intervals to enable a more accurate control of the emulsion than was previously possible by the procedure of manually drawing a sample of the emulsion for determination of the ESI. A more accurate control of the emulsion results in a more uniform mill product and a substantial saving in both oil and emulsifier.

While I have disclosed and described preferred embodiments of my invention, I wish it understood that I do not intend to be restricted solely thereto, but rather that I do intend to include all embodiments thereof which would be apparent to one skilled in the art and which come within the spirit and scope of my invention.

I claim:

1. A method of controlling the stability of an oil-in-water emulsion suitable for use as a lubricant in a metalworking operation comprising the steps of, circulating a portion of the emulsion through a liquid density measuring cell and operating the cell to generate a first electric signal proportional to the density of the emulsion flowing through the cell, periodically interrupting the flow of the emulsion through the cell and maintaining a quantity of the emulsion in the cell in a quiescent state for a predetermined time sufficient to permit the oil and water phases of the emulsion to at least partially separate, operating the cell to determine the density of the emulsion in the cell at the termination of the predetermined time and to generate a second electric signal proportional to the determined density of the at least partially separated emulsion, and comparing the first and second electric signals to determine the change of density of the liquid in the cell during the predetermined time and utilizing the determined change of density as an indication of emulsion stability.

2. The method of claim 1 wherein the step of utilizing the change in determined density comprises determining the emulsion stability index of the emulsion, and providing a digital readout displaying the determined index.

3. The method of claim 1 wherein the step of utilizing the determined change of density comprises determining the emulsion stability index of the emulsion, comparing the determined emulsion stability index with a desired emulsion stability index, and controlling the addition of an emulsifying agent to the emulsion in response to a predetermined minimum deviation between the determined and desired indexes.

4. The method of claim 3 wherein the step of controlling the addition of an emulsifying agent to the emulsion comprises adding a metered quantity of an emulsifying agent into a reservoir containing the emulsion.

5. The method of claim 1 wherein the oil-in-water emulsion is maintained in a system including a reservoir containing a quantity of emulsion and means for circulating the emulsion from the reservoir to the metalworking operation and for returning the used emulsion from the metalworking operation to the reservoir, and wherein the method further comprises adding water to the reservoir to maintain a predetermined level of liquid in the reservoir, and periodically adding oil to the reservoir as required to maintain the desired concentration of oil in the emulsion.

6. The method of claim 5 wherein the step of utilizing the determined change of density comprises determining the emulsion stability index of the emulsion, comparing the determined emulsion stability index with a desired emulsion stability index, and controlling the addition of an emulsifying agent to the emulsion when the deviation between the determined and desired indexes exceeds a predetermined minimum.

7. The method of claim 5 wherein the step of controlling the addition of an emulsifying agent to the emulsion comprises adding a metered quantity of an emulsifying agent to the oil which is periodically added to the emulsion in the reservoir.

8. The method of claim 7 further comprising the step of providing a digital readout of the determined ESI.

9. The method of claim 1 further comprising the step of providing a substantially continuous recording of determined density of the emulsion while the emulsion is being circulated through the density measuring cell.

10. The method of claim 9 wherein the step of providing a substantially continuous recording comprises recording a trace of said first electric signal on a continuous recorder, and calibrating the recorder to represent the determined density as the concentration of oil in the emulsion in percent of oil.

11. The method of claim 10 further comprising the step of comparing the percent of oil in the emulsion as determined by the density cell with a desired percentage of oil, and controlling the addition of oil to the emulsion in response to deviation of the measured percent of oil from the desired percent of oil.

12. The method of claim 1 further comprising the step of conducting the first electric signal to a strip chart recorder to provide a continuous recording of the density of the emulsion determined by the density cell, and employing the recorder to compare the determined density with a selected set point representing the desired emulsion density.

13. The method of claim 12 further comprising the step of controlling the addition of oil to the emulsion in response to the comparison of the measured density with the selected set point.

14. A method of controlling the stability of an oil-in-water emulsion suitable for use as a lubricant in a metalworking operation comprising the steps of, providing a measuring cell including a U-shaped tube mounted in a substantially vertical direction with the open end of the "U" being rigidly supported and the closed loop end unsupported, flowing a portion of the emulsion through the U-shaped tube, determining the density of the emulsion flowing through the U-shaped tube by exciting the unsupported end of the tube at a constant frequency and generating a first electric signal which is a function of the tube displacement, periodically interrupting the flow of the emulsion through the cell and maintaining a quantity of the emulsion in the cell in a quiescent state for a predetermined time sufficient to permit the oil and water phases of the emulsion in the U-shaped tube to at least partially separate, operating the cell to determine the density of the emulsion in the cell at the termination of the predetermined time and to generate a second electric signal proportional to the determined density of the at least partially separated emulsion, and comparing the first and second electric signals to determine the change of density of the liquid in the cell during the predetermined time and utilizing the determined change of density as an indication of emulsion stability.

15. The method of claim 14 wherein the density measuring cell is mounted with the opposed legs of the U-shaped tube extending substantially vertical and with the closed loop end at the top so that separation of the oil and water phases results in a decreased density reading.

16. The method of claim 15 wherein the step of utilizing the determined change of density comprises determining the emulsion stability index of the emulsion, comparing the determined emulsion stability index with a desired emulsion stability index, and controlling the addition of an emulsifying agent to the emulsion in response to a predetermined deviation between the determined and desired indexes.

17. The method of claim 16 wherein the step of controlling the addition of an emulsifying agent to the emulsion comprises adding a metered quantity of an emulsifying agent into a reservoir containing the emulsion.

18. The method of claim 14 wherein the oil-in-water emulsion is maintained in a system including a reservoir containing a quantity of emulsion and means for circulating the emulsion from the reservoir to the metalworking operation and for returning the used emulsion from the metalworking operation to the reservoir, and wherein the method further comprises adding water to the reservoir to maintain a predetermined level of liquid in the reservoir, and periodically adding oil to the reservoir as required to maintain the desired concentration of oil in the emulsion.

19. The method of claim 18 wherein the step of utilizing the determined change of density comprises determining the emulsion stability index of the emulsion, comparing the determined emulsion stability index with a desired emulsion stability index, and controlling the addition of an emulsifying agent to the emulsion when the deviation between the determined and desired indexes exceeds a predetermined minimum.

20. The method of claim 19 wherein the step of controlling the addition of an emulsifying agent to the emulsion comprises adding a metered quantity of an emulsifying agent to the oil which is periodically added to the emulsion in the reservoir.

21. The method of claim 20 wherein the step of utilizing the change in determined density comprises determining the emulsion stability index of the emulsion, and providing a digital readout displaying the determined index.

22. A method of controlling the oil concentration in an oil-in-water emulsion suitable for use as a lubricant in a metalworking operation comprising, the steps of circulating a portion of the emulsion through a liquid density measuring cell and operating the cell to generate a first electric signal proportional to the density of the emulsion flowing through the cell, conducting the first electric signal to a continuous recorder and operating the recorder to provide a continuous record of the measured density and to compare the measured density with a predetermined desired density, generating a second electric signal in response to the detection of a predetermined minimum deviation between the measured density the desired density, and utilizing said second electric signal to control the addition of make-up oil to the emulsion to automatically maintain the oil concentration of the emulsion within predetermined limits periodically interrupting the flow of emulsion through the cell while maintaining a quantity of the emulsion in the cell for a predetermined time sufficient to permit the oil and water phases of the emulsion to at least partially separate comparing the density of the emulsion in the cell at the beginning and end of the predetermined times to determine the density change due to separation of the oil and water phases, and utilizing the determined density change as an indication of emulsion stability.

23. The method of claim 22 further comprising the steps of controlling the addition of an emulsifying agent to the emulsion in response to the determined density change.

* * * * *